| United States Patent [19] | [11] Patent Number: 5,011,311 |
| Harris et al. | [45] Date of Patent: Apr. 30, 1991 |

[54] DENTAL ALLOY

[76] Inventors: Brian C. Harris, 8 Garth Road, Kingston upon Thames, Surrey, England, KT2, 5NY; Raymond Cook, Flat 3, 68 Southcote Road, Bournemouth, England, BH1 3SS

[21] Appl. No.: 400,594

[22] Filed: Aug. 29, 1989

[30] Foreign Application Priority Data

Aug. 31, 1988 [GB] United Kingdom ................ 8820552
Jun. 27, 1989 [GB] United Kingdom ................ 8914689

[51] Int. Cl.$^5$ .................... C22C 5/04; B32B 17/06; B32B 15/00; A61C 13/08
[52] U.S. Cl. .................... 400/208; 433/207; 428/433; 428/450; 420/463; 420/464
[58] Field of Search ................ 420/464; 428/450, 433; 433/207, 208

[56] References Cited

U.S. PATENT DOCUMENTS

| 4,551,302 | 11/1985 | Wagner et al. | 420/464 |
| 4,608,229 | 8/1986 | Lanam et al. | 420/464 |
| 4,836,984 | 6/1989 | Wagner et al. | 420/464 |

FOREIGN PATENT DOCUMENTS 3239338 2/1984 Fed. Rep. of Germany .

*Primary Examiner*—Theodore Morris
*Assistant Examiner*—Robert R. Koehler

[57]  ABSTRACT

A dental alloy consists essentially of 60 to 85% by weight palladium, 5 to 20% by weight copper, 3 to 15% by weight gallium, and, as modifiers, 0.5 to 7% by weight gold, 0.005 to 0.02% by weight ruthenium, rhenium, iridium or a mixture of at least two of these metals, 1 to 5% by weight tin and 0 to 2% by weight nickel, wherein the sum of the modifiers is from 5.5 to 10% by weight. Dental restorations are produced by firing ceramic onto at least part of the surface of a casting of such an alloy.

12 Claims, No Drawings

DENTAL ALLOY

FIELD OF THE INVENTION

The present invention relates to a palladium-based gold-containing alloy and, in particular, to such an alloy to which a ceramic surface may be applied for the production of dental restorations.

BACKGROUND OF THE INVENTION

It is well known to prepare caps, crowns, bridges, inlays and other dental restorations from alloy castings, to which a porcelain or like ceramic surface is applied and then bonded, as by firing, in order to reproduce the function, colour and shape of natural teeth.

The alloys used in such work are expected to satisfy a number of requirements. Thus, in addition to being physiologically acceptable for long-term use in the mouth, the alloys should exhibit sufficient compressive strength in order to withstand the force exerted thereon during mastication; a Vickers Hardness of at least 150 is generally required. The alloy should also have a liquidus temperature which is low enough for it to be cast with the equipment normally found in dental laboratories, whilst exhibiting a solidus which is sufficiently high to withstand the ceramic-firing temperature and to permit the alloy to be soldered, if necessary. The alloy should generally, therefore, exhibit a liquidus of not more than 1400° C. and a solidus of at least 1100° C.

The alloys ideally should also have sufficient tensile elongation (in general, at least 2% and preferably at least 4%) to permit marginal adjustment after placement in the mouth and should also have a coefficient of thermal expansion such that the ceramic coating is subjected to moderate compression as it cools from the elevated temperature at which it was fired, since this improves the bond strength of the resultant restoration or prosthesis. In general, a coefficient of thermal expansion of from 0.66 to 0.72 percent at 500° C. is desirable for compatibility with commercially available dental porcelains.

Needless to say, the alloy should also provide a firm bond to the ceramic applied thereto and should not give rise to discoloration of the ceramic surface.

Until recently, alloys of gold and platinum had been used as dental alloys. However, as the prices of these metals have risen, alternatives have been sought.

Palladium/silver alloys have been developed which have exhibited the required workability and porcelain-bonding properties but these have proved unsatisfactory, owing to their tendency to discolour the dental porcelain applied thereto.

GB-A-2,118,971 discloses a dental alloy consisting substantially of 50 to 85% palladium; 5 to 40% copper, cobalt or a mixture thereof; 1 to 15% gallium; up to 5% of a modifier selected from nickel, gold, indium, ruthenium, tin and mixtures thereof; up to 1% boron; and up to 0.5% of a grain refiner selected from rhenium, iridium and mixtures thereof (the percentages being by weight). This British patent specification teaches (page 2, lines 31–33) that an amount of modifier metal in excess of 5% would adversely affect the balance of properties of the alloy and should not be employed.

US-A-4,608,229, however, teaches that it is possible to incorporate the modifier metal into certain palladium/copper/gallium alloys in an amount in excess of 5%, whilst still obtaining a low-cost dental alloy casting having a fracture-resistant, non-dendritic structure with acceptable Vickers Hardness, good ductility and excellent porcelain bond strength. Specifically, this US patent discloses an alloy that consists essentially of 60 to 85% palladium, 5 to 20% copper, 3 to 15% gallium and, as modifiers, 0.5 to 2% gold, 3.2 to 6% indium, 0.005 to 0.02% ruthenium, 0 to 2% tin and 0 to 2% nickel, the sum of the concentrations of the modifiers being greater than 5.5% and up to 8.5% (the percentages being by weight).

It has been found, however, that alloys within the composition defined in US-A-4,608,229 have a tendency to cause the formation of bubbles in the dental ceramic during the firing stage. Although this tendency can be lessened by the application of a high level of expertise by the dental technician, it would clearly be desirable to develop an alloy which does not show this tendency and which, therefore, places less of a demand upon the skill of the dental technician.

The alloys disclosed in US-A-4,608,229 have also been found to exhibit variable workability.

SUMMARY OF THE INVENTION

Unexpectedly, the tendency to cause bubbles in the porcelain exhibited by alloys according to US-A-4,608,229 has been found to be due to the presence of indium in the alloys. It has also been found that it is possible to provide an alloy that is essentially free from indium and yet Which has good porcelain-bonding characteristics, workability and Vickers Hardness.

In particular, the present invention provides an alloy that consists essentially of 60 to 85% by weight palladium, 5 to 20% by weight copper, 3 to 15% by weight gallium, 0.5 to 7% by weight gold, 1 to 5% by weight tin, 0 to 2% by weight nickel, and 0.005 to 0.02% by weight of a grain refiner selected from the group consisting of ruthenium, rhenium, iridium and mixtures of at least two of these three metals, wherein the sum of the amounts of gold, tin, nickel, ruthenium, rhenium and iridium is 5.5 to 10% by weight.

The present invention also provides a dental restoration comprising a casting of an alloy according to this invention and a ceramic coating (which term includes a ceramic jacket) bonded to at least part of the surface of the casting.

DESCRIPTION OF PREFERRED EMBODIMENTS

The palladium, copper and gallium are considered to be the base or primary components of the alloy whereas the gold, tin, ruthenium, rhenium, iridium and nickel are regarded as modifiers.

The palladium (Pd) is present preferably in an amount of from 68 to 82%, more preferably 76.8 to 78.8%, by weight of the alloy. The copper (cu) is preferably present in an amount of 8 to 16%, more preferably 11 to 12%, by weight of the alloy. The gallium (Ga) is present usually in an amount of up to 10%, preferably from 3.5 to 8%, more preferably 4.5 to 5.5%, by weight of the alloy.

The gold (Au) is usually present in an amount of up to 6%, preferably up to 5.5%, more preferably from 2 to 5%, and most preferably from 3.5 to 4.5%, by weight of the alloy. The tin (Sn) is preferably present in an amount of 1.1 to 3.7%, more preferably 1.2 to 2.2%, by weight of the alloy. Nickel (Ni) is, as indicated above, an optional component of the present alloys. However, as nickel can cause an allergic reaction in some people, it will usually be used in a comparatively small amount, e.g. up to 1% by weight of the alloy, more probably not more than 0.5% by weight, and can be dispensed with altogether.

Amongst the modifier metals, the ruthenium (Ru), rhenium (Re) and iridium (Ir), or the mixtures thereof, are considered to act as grain refiners, for they are believed to promote reduced, uniform grain size in the structures cast from the alloy. Ruthenium is particularly preferred and will usually be used in the substantial absence of rhenium and iridium. As in US-A-4,608,229, the amount of grain refiner is typically 0.006 to 0.012% by weight.

The total concentration in the alloy of the modifiers (Au, Sn, Ru, Re, Ir, Ni) is preferably from 5.5 to 8.5%, more preferably 5.5 to 7.7%, by weight of the alloy.

The alloys according to the present invention may be prepared using conventional procedures, in general by mixing the component metals (conveniently in subdivided form such as granules, beads or powder) in the appropriate proportions and melting them together in an appropriate vessel, e.g. a crucible. Fusion of the metals can be effected using an induction, gas-fired or other suitable furnace and the metals are usually fused under vacuum or a blanket of hydrogen.

The starting metals will normally be of a purity consistent with the intended use of the alloy in prosthodontics. Any element present as an impurity should not be deleterious either to the production or to the use of the dental alloy and normally should not be present in an amount exceeding 0.005% by weight.

The addition of substances to improve the alloying process comes into consideration, provided that deleterious residues are not left in the alloy. For example, a small amount of boron (e.g. as a boride) may be added to act as a scavenger for oxides formed during the alloying process; however, the boron should oxidise during the scavenging process and either volatilise or separate out from the alloy in a slag.

Normally, the alloy is cast and worked into ingots (typically of 1-2g) for sale to the dental profession, although other forms, such as grains, would also be usable.

The alloy may be used to make a dental restoration by any of the conventional techniques. Normally, the alloy is melted and poured into a mould that has been prepared using the lost-wax process, which mould may be mounted in a centrifugal casting machine. After cooling, the casting is removed from the mould and then prepared for the application of a dental ceramic, usually a dental porcelain, by the customary firing techniques. Normally, the ceramic is prepared as a slurry which is applied to the alloy casting, as by painting, and then fired. Usually, a first, opaque layer is applied, followed optionally by a second opaque layer and then by a so-called dentine porcelain layer, after which a final glaze is applied. The opaque layer or layers are employed in order to conceal the colour of the metal alloy and to form a metal-to-ceramic bond.

The alloy of the present invention has an excellent workability and can even be subjected to cold rolling. Improvements in workability in dental alloys are normally considered to have an adverse effect on toughness characteristics; however, the alloy of the present invention is characterised by an excellent balance of workability and toughness characteristics. The alloy of the present invention, being essentially silver-free, has not been found to discolour the dental ceramics applied to it; furthermore, the alloy of this invention has not been found to cause bubbling of the porcelain during the firing stage. The present alloy has also been found to exhibit satisfactory solidus and liquidus temperatures, ductility and Vickers Hardness, and is relatively inexpensive The present invention is illustrated in and by the following example.

EXAMPLE 1

A number of alloys were prepared—in conventional manner, by mixing the ingredients together and melting the mixture in a furnace—using palladium, copper and gallium as the primary components, with the addition of various modifier metals, in accordance with the compositions specified in Table 1 hereinafter. Alloys H, I and J are in accordance with the present invention, alloys A to G being for comparison purposes.

All alloys were cast into wire bars and rolled to form wire and strip. The wire was used in a hardened and in a softened condition to determine the mechanical properties. The production of strip was used both as a test of the workability of the alloy and to produce cropped pieces for porcelain bonding trials.

The mechanical properties of the alloys were determined using an Instron (trade mark) Tensile Tester for tensile properties and a Vickers hardness tester for hardness properties. The results are given in Table 2 hereinafter. In Table 2, 'UTS' stands for ultimate tensile strength.

For the porcelain bonding trials pieces of strip were cleaned by stone grinding followed by microblasting with alumina and degreasing in an ultrasonic bath. The pieces were then oxidised in air at 1010° C. for 10 minutes, the oxide was removed by microblasting and this was followed by ultrasonic cleaning. This oxidation/microblasting process was then repeated to produce pieces for porcelain bonding. Two commercially available dental porcelains were used, supplied respectively under the tradenames Vita and Biodent. First, two layers of opaque porcelain were applied to the cleaned alloy surface as a slurry. The opaque material was allowed to dry before firing under vacuum for 3 minutes at 960° C. for Vita VMK 88, or 980° C. for Biodent Universal. A single dentine layer was then applied to the opaque layers and fired under vacuum for 3 minutes at 900° C. for Vita VMK 68, or 980° C. for Biodent Universal. Finally a glaze was applied and fired in air at 960° C.

Referring to Table 1, the alloy A, which has a composition in accordance with the teaching in US-A-4,608,229, was very tough and consequently difficult to work down to a strip.

By reducing the copper content and increasing the content of palladium a more workable alloy, B, was produced; this alloy, however, was shown to exhibit bubbling during the bonding of the opaque porcelain.

Alloys C, D and E have compositions in accordance with the teaching in GB-A-2,118,971. Although the in-service properties of alloy C were, for the most part, acceptable, it was difficult to work the alloy down to strip; alloy D was also considered to be too tough. Alloy E did not exhibit any bonding problems and was workable down to a strip.

By increasing the modifier content to 5.7% with the addition of indium, a workable alloy, F, was produced; this alloy, however, caused bubbling in the opaque porcelain. Alloy G, with an increased content of indium though workable, exhibited worse bubbling than alloy F.

By substituting indium in the composition of alloy F with tin, a workable alloy H was produced which was shown to have acceptable mechanical properties and which did not cause bubbling of the porcelain. Alloys I and J had higher contents of gold and lower contents of gallium and tin than alloy H but they still exhibited acceptable mechanical properties and did not cause porcelain bubbling.

From Table 1, it may be concluded that in high-palladium gold-containing alloys, indium plays a role in causing bubble formation during the firing of opaque porcelain to the alloy surface. By omitting indium and substituting tin for it, this undesirable property can be eliminated, permitting the production of alloys that have a high content of palladium and modifier metals and that can be used as dental bonding alloys.

It will, of course, be understood that the present invention has been described above purely by way of example, and that modifications of detail can be made within the scope of the invention.

TABLE 1

| Alloy | Composition (% by weight) | | | | | | | Porcelain Bonding | Melting Range (°C.) | Density (g · cm$^{-3}$) |
| --- | --- | --- | --- | --- | --- | --- | --- | --- | --- | --- |
| | Pd | Au | Ru | Cu | Ga | In | Sn | | | |
| A | 76.19 | 1.80 | 0.01 | 10.00 | 7.00 | 5.00 | — | Acceptable | 1120–1180 | 10.7 |
| B | 78.19 | 1.80 | 0.01 | 8.00 | 7.00 | 5.00 | — | Bubbling | 1180–1220 | 10.5 |
| C | 77.80 | 1.80 | 0.01 | 10.00 | 10.39 | — | — | Acceptable | — | — |
| D | 77.80 | 2.19 | 0.01 | 10.00 | 10.00 | — | — | — | 1080–1180 | 11.3 |
| E | 77.80 | 2.19 | 0.01 | 15.00 | 5.00 | — | — | Acceptable | 1260–1280 | 11.4 |
| F | 77.80 | 3.99 | 0.01 | 11.50 | 5.00 | 1.70 | — | Bubbling | — | 11.6 |
| G | 77.80 | 2.19 | 0.01 | 11.50 | 5.00 | 3.50 | — | Bubbling | — | 11.4 |
| H | 77.80 | 3.99 | 0.01 | 11.50 | 5.00 | — | 1.70 | Acceptable | 1190–1270 | 10.5 |
| I | 77.80 | 5.99 | 0.01 | 11.50 | 3.50 | — | 1.20 | Acceptable | 1370–1405 | 11.8 |
| J | 77.80 | 4.99 | 0.01 | 11.50 | 4.20 | — | 1.50 | Acceptable | 1250–1380 | 11.7 |

TABLE 2

| ALLOY | HARDENED | | | | SOFTENED | | | |
| --- | --- | --- | --- | --- | --- | --- | --- | --- |
| | HARDNESS (HV) | YIELD STRESS (kg · mm$^{-2}$) | UTS (kg · mm$^{-2}$) | ELONGATION (%, 10 cm) | HARDNESS (HV) | YIELD STRESS (kg · mm$^{-2}$) | UTS (kg · mm$^{-2}$) | ELONGATION (%, 10 cm) |
| A | 411 | 75 | 105 | 16 | 351 | 69 | 98 | 19 |
| B | 301 | — | — | — | 284 | 74 | 99 | 23 |
| D | 468 | 102 | 152 | 3 | 313 | 89 | 107 | 18 |
| E | 367 | 82 | 125 | 3 | 210 | 56 | 64 | 32 |
| F | — | — | — | — | 208 | — | — | — |
| G | — | — | — | — | 249 | 45 | 70 | 36 |
| H | 375 | 61 | 107 | 4 | 220 | 37 | 63 | 30 |
| I | 310 | 45 | 90 | 3 | 190 | 21 | 62 | 35 |
| J | 300 | 37 | 91 | 6 | 195 | 32 | 65 | 34 |

We claim:

1. A dental alloy consisting essentially of 60 to 85% by weight palladium, 5 to 20% by weight copper, 3 to 15% by weight gallium, 0.5 to 7% by weight gold, 1 to 5% by weight tin, 0 to 2% by weight nickel, and 0.005 to 0.02% by weight of a grain refiner selected from ruthenium, rhenium, iridium and mixtures of at least two of these metals, wherein the sum of gold, tin, nickel, ruthenium, rhenium and iridium is from 5.5 to 10% by weight.

2. An alloy according to claim 1, wherein the alloy contains 68 to 82% by weight palladium, 8 to 16% by weight copper, 3.5 to 8% by weight gallium, 1.1 to 3.7% by weight tin, 0 to 2% by weight nickel, and 0.005 to 0.02% by weight ruthenium, rhenium, iridium or a mixture of at least two of these metals, wherein the sum of gold, tin, nickel, ruthenium, rhenium and iridium is from 5.5 to 8.5% by weight.

3. An alloy according to claim 1, wherein the alloy contains 76.8 to 78.8% by weight palladium, 11 to 12% by weight copper, 4.5 to 5.5% by weight gallium, 1.2 to 2.2% by weight tin, 0 to 2% by weight nickel, and 0.005 to 0.02% by weight ruthenium, rhenium, iridium or a mixture of at least two of these metals, wherein the sum of gold, tin, nickel, ruthenium, rhenium and iridium is from 5.5 to 7.7% by weight.

4. An alloy according to claim 1, wherein the alloy contains from 0.5 to 5.5% by weight gold.

5. An alloy according to claim 2, wherein the alloy contains from 2 to 5% by weight gold.

6. An alloy according to claim 3, wherein the alloy contains 3.5 to 4.5% by weight gold.

7. An alloy according to claim 1 which is essentially nickel-free.

8. An alloy according to claim 4 which is essentially nickel-free.

9. An alloy according to claim 1 wherein the grain refiner is ruthenium.

10. An alloy according to claim 4 wherein the grain refiner is ruthenium.

11. A dental restoration comprising a casting of an alloy according to claim 1 and a ceramic coating bonded to at least part of the surface of the casting.

12. A dental restoration comprising a casting of an alloy according to claim 4 and a ceramic coating bonded to at least part of the surface of the casting.

* * * * *